United States Patent [19]

Joy

[11] Patent Number: 4,593,569

[45] Date of Patent: Jun. 10, 1986

[54] ULTRASONIC TRANSDUCER UNIT TO LOCATE CRACKS IN RAIL BASE

[76] Inventor: Ivan L. Joy, 4137 Lower Silver Lake Rd., Topeka, Kans. 66618

[21] Appl. No.: 525,002

[22] Filed: Aug. 22, 1983

[51] Int. Cl.[4] ............................................. G01N 29/04
[52] U.S. Cl. ........................................ 75/636; 73/639
[58] Field of Search ................. 73/628, 629, 636, 639, 73/641

[56] References Cited

U.S. PATENT DOCUMENTS

| | | | |
|---|---|---|---|
| 2,672,753 | 3/1954 | Drake | 73/67 |
| 2,678,559 | 5/1954 | Drake | 73/67 |
| 3,028,751 | 4/1962 | Joy | 73/67.8 |
| 3,028,753 | 4/1962 | Joy | 73/67.8 |
| 3,122,661 | 2/1964 | Joy | 310/8.7 |
| 3,156,111 | 11/1964 | Joy | 73/67.9 |
| 3,166,731 | 1/1965 | Joy | 340/15 |
| 3,218,846 | 11/1965 | Joy | 73/71.5 |
| 3,251,220 | 5/1966 | Joy | 73/67.7 |
| 4,143,553 | 3/1979 | Martens et al. | 73/641 |
| 4,165,648 | 8/1979 | Pagano | |
| 4,487,071 | 12/1984 | Pagano et al. | 73/636 |

*Primary Examiner*—Stewart J. Levy
*Assistant Examiner*—John E. Chapman, Jr.
*Attorney, Agent, or Firm*—D. A. N. Chase; Michael Yakimo, Jr.

[57] ABSTRACT

Apparatus for ultrasonic detection of flaws in the rail base of a track rail includes a sliding shoe having a transducer unit and coupling medium reservoir mounted thereon. The transducer, which is part of an ultrasonic testing system, transmits search signals into the rail base and receives associated reflected signals thereof. These signals, being capable of pictorially representing defects in the base of the rail, are monitored by the tester. The preferred embodiments allow for relative movement of the transducer unit and coupling medium reservoir along the base of the rail in order to provide for a succession of transmitted and reflected signals along the longitudinal extent of the rail base so as to test for flaws, defects, etc. in the same.

20 Claims, 10 Drawing Figures

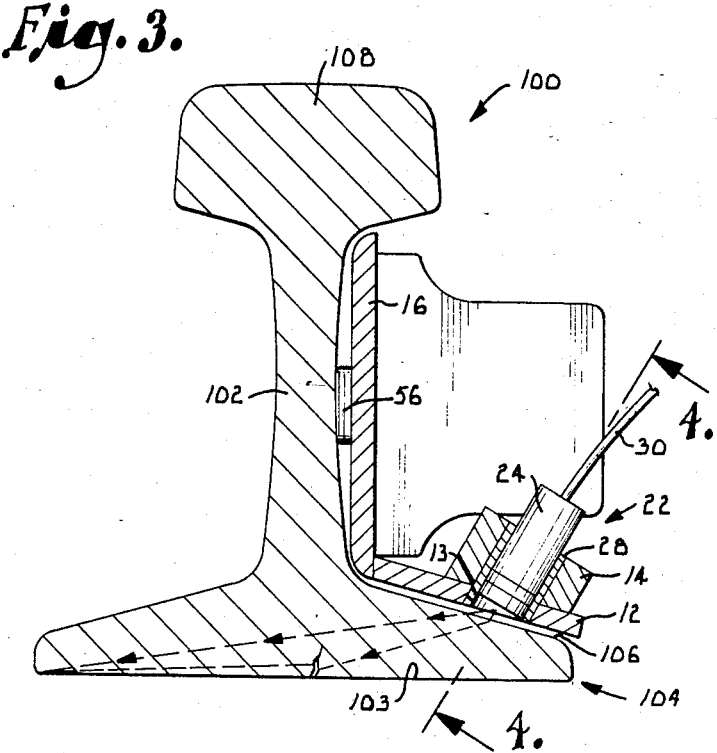
Fig. 3.
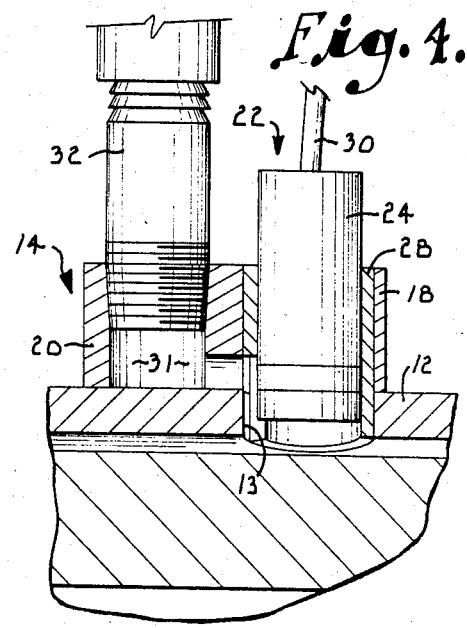
Fig. 4.
Fig. 5.
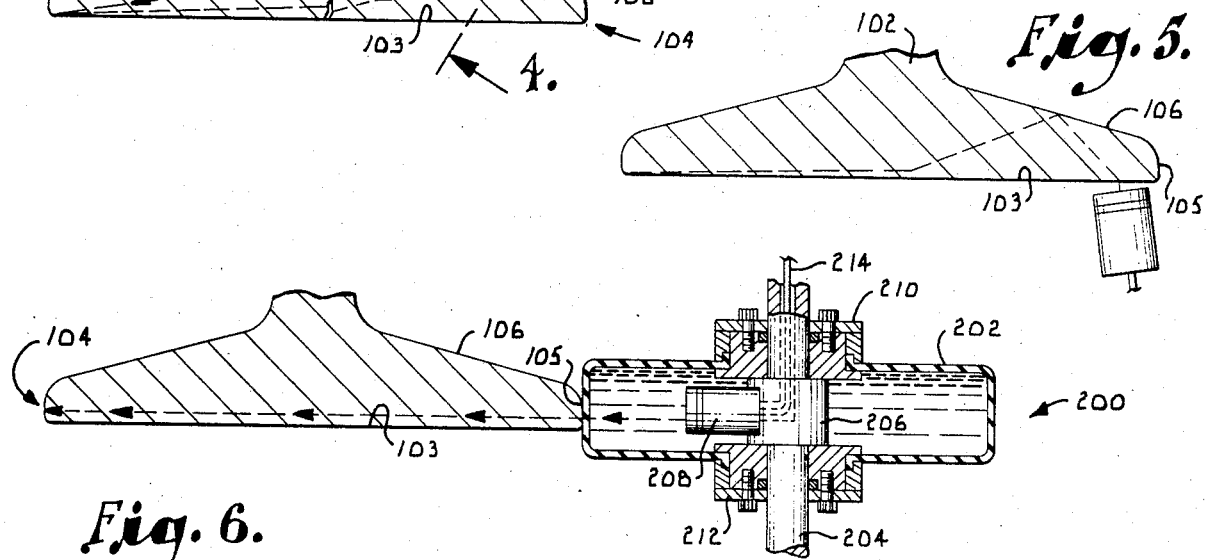
Fig. 6.
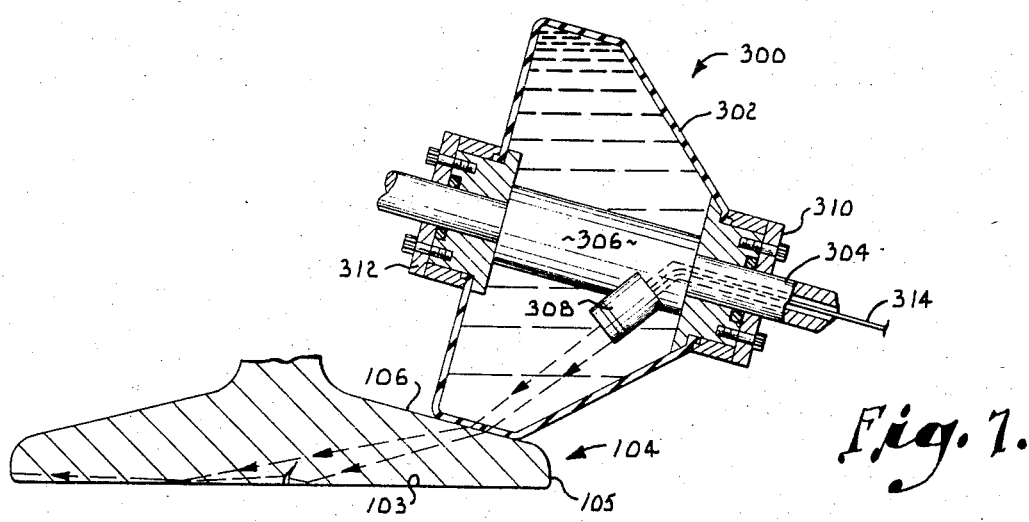
Fig. 7.

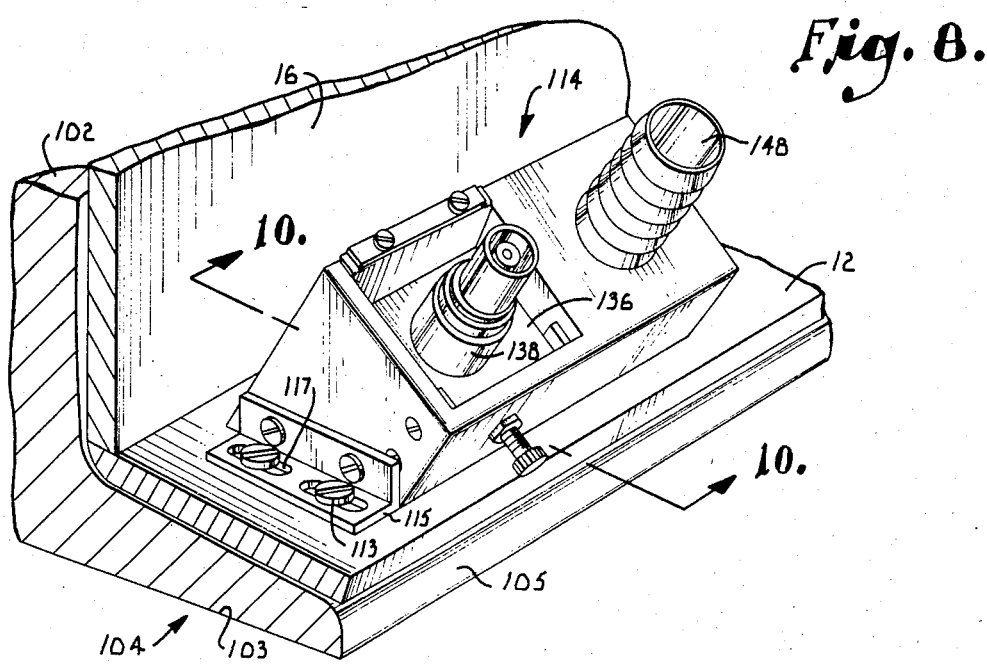
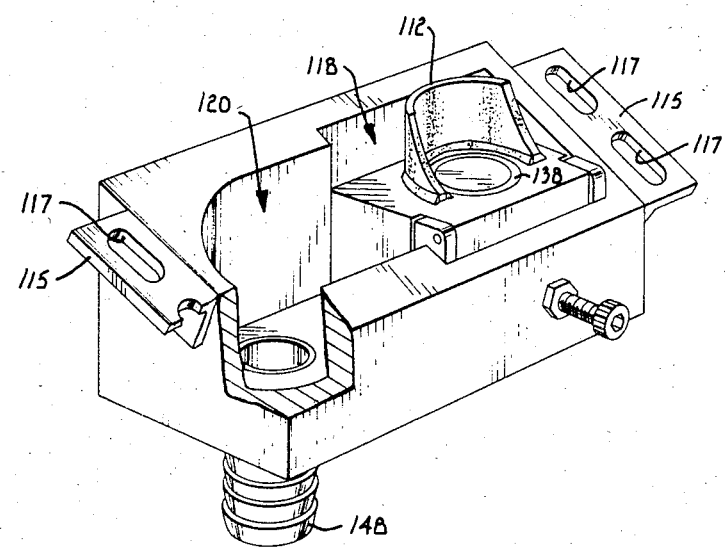
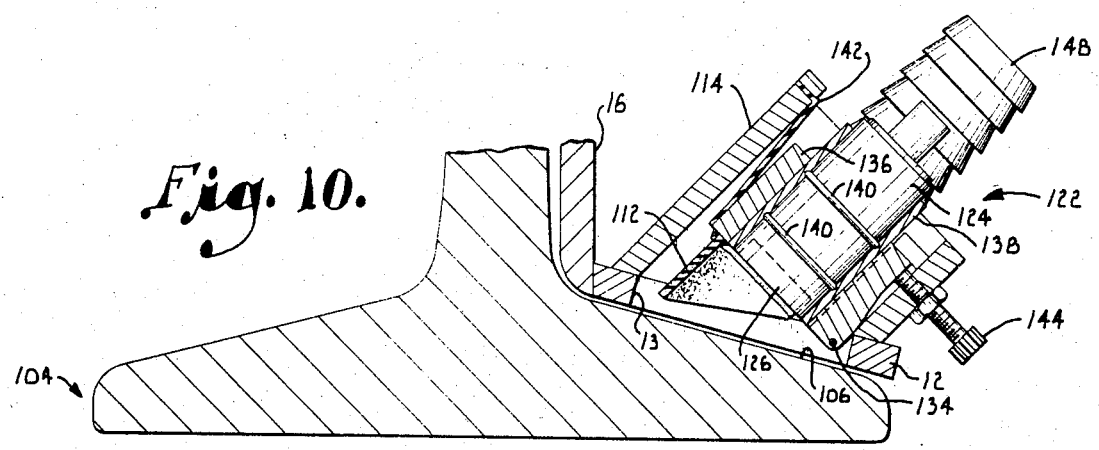

ULTRASONIC TRANSDUCER UNIT TO LOCATE CRACKS IN RAIL BASE

BACKGROUND OF THE INVENTION

This invention relates to ultrasonic testing devices, and more particularly, to a method and apparatus for detecting flaws, cracks and the like along the base of a track rail.

Ultrasonic testing of track rails utilizes ultrasonic vibrations, as generated by an electro-acoustic transducer in the form of a piezo-electric quartz crystal, which is electrically energized at high frequency for conversion of the electrical oscillations into mechanical oscillations. The crystal engages the rail through a fluid couplant and is moved along the extent of the track rail. Heretofore, resulting ultrasonic search beams have been directed through the web and running surface of the rail under test with at least the associated reflected beams being monitored to determine whether the transmitted beams encountered any flaws in the tested areas. Generally speaking, a reflected signal of the same strength as the transmitted signal indicates a flawless rail with a weakening of the reflected or return signal associated with the transmitted signal indicating internal flaws within the rail. There are various means for monitoring the transmitted and reflected beams/signals, one such means being shown by my U.S. Pat. No. 3,156,111 which is hereby incorporated by reference herein. In this patent, transmitted and echo signals are represented on a cathode ray tube that are readily understandable pictorial representations of certain internal structural characteristics of a track rail.

In the past, flaw testing has been concentrated on the top running surface of the rail and the web extending therebetween. However, the manufacturers of such rails are now using roller-type straightners to straighten the rails so as to expedite production. These straightening devices may produce flaws, cracks etc., in the bottom of the base of the rail usually first recognizable only after the track rail has been put into service. Thus, it is now desirable to have a method for predetection of such flaws in the base of the rail utilizing ultrasonic testing techniques and performing apparatus to easily effect such testing.

Accordingly, I have invented methods and accompanying apparatus designed to detect flaws, cracks etc., in the base of the rail particularly along the bottom surface thereof. Generally, my apparatus comprises a sliding shoe relatively movable along the top surface of the base of the rail which is adjacent the web thereof. Mounted on the sliding shoe in movement therewith is a transducer element along with fluid means for providing a wedge of water between the transducer and the top surface of the rail which acts as the ultrasonic coupling medium therebetween. The coupling medium cooperates with the user-selectable orientation of the transducer unit relative to the top surface of the rail base so as to transmit ultrasonic waves throughout the rail base particularly along the bottom surface thereof. Base echoes and return echoes, corresponding to the transmitted and reflected signals, are displayed on a cathode ray tube in a manner as set forth in my above-identified patent so that a visual inspection can be made of these signals to determine the absence or presence of defects in the rail base. The relative movement of the apparatus along the extent of the rail provides for a succession of such transmitted and reflected signals and thus a continuous testing therealong.

Accordingly, it is a general object of this invention to provide a method and performing apparatus for detecting defects in the base of a track rail.

Another object of this invention, as aforesaid, is to provide apparatus for housing an electromechanical transducer and coupling medium in relative movement along the base of the rail so as to transmit and receive ultrasonic signals relative therealong.

Still another object of this invention, as aforesaid, is to provide apparatus which continuously interposes said coupling medium between the transducer and the surface of the rail base.

A more particular object of this invention is to provide apparatus, as aforesaid, at which the angle of the entry of the ultrasonic signal, as emitted by the transducer relative to the rail base, is operator-adjustable to assure that the ultrasonic waves scrub the bottom surface of the rail base.

Other objects and advantages of this invention will become apparent from the following description taken in connection with the accompanying drawings, wherein is set forth by way of illustration and example, embodiment of this invention.

BRIEF DESCRIPTION OF THE DRAWINGS

FIG. 3 is a sectional elevation view, taken along line 3—3 in FIG. 1, and showing the relationship of the mounting and sliding plates of the detection assembly with the web and top surface of the base of the rail.

FIG. 4 is a sectional view, taken along line 4—4 in FIG. 3, and showing the coupling fluid flow means and transducer unit mounted in the housing on the sliding shoe.

FIG. 5 is a diagrammatical view showing an alternative disposition of the transducer unit relative to the bottom surface of the base of the rail so as to scrub the base surface thereof with ultrasonic signals.

FIG. 6 is a transverse sectional view along the diameter of a fluid filled wheel, except for the interior elements thereof, of an alternative embodiment illustrating a transducer unit mounted in said fluid-filled wheel and normally disposed to the side wall of the base of the rail.

FIG. 7 is a central sectional view of another alternative embodiment along the diameter of a fluid-filled wheel, save for the interior elements thereof, showing a transducer unit mounted in said fluid-filled wheel and disposed relative to the top surface of the base of the rail.

FIG. 8 is a perspective fragmentary view showing the preferred embodiment of the housing of FIG. 4 with the transducer unit and coupling fluid flow assembly mounted therein.

FIG. 9 is a view of the housing of FIG. 8 from the bottom side thereof with a portion of the housing broken away to show the coupling compartment therein.

FIG. 10 is a sectional view, taken along line 10—10 in FIG. 8, and showing the means for changing the angle of inclination of the housing and transducer unit mounted therein relative to the top surface of the rail base.

DESCRIPTION OF THE PREFERRED EMBODIMENTS

Figure 1:
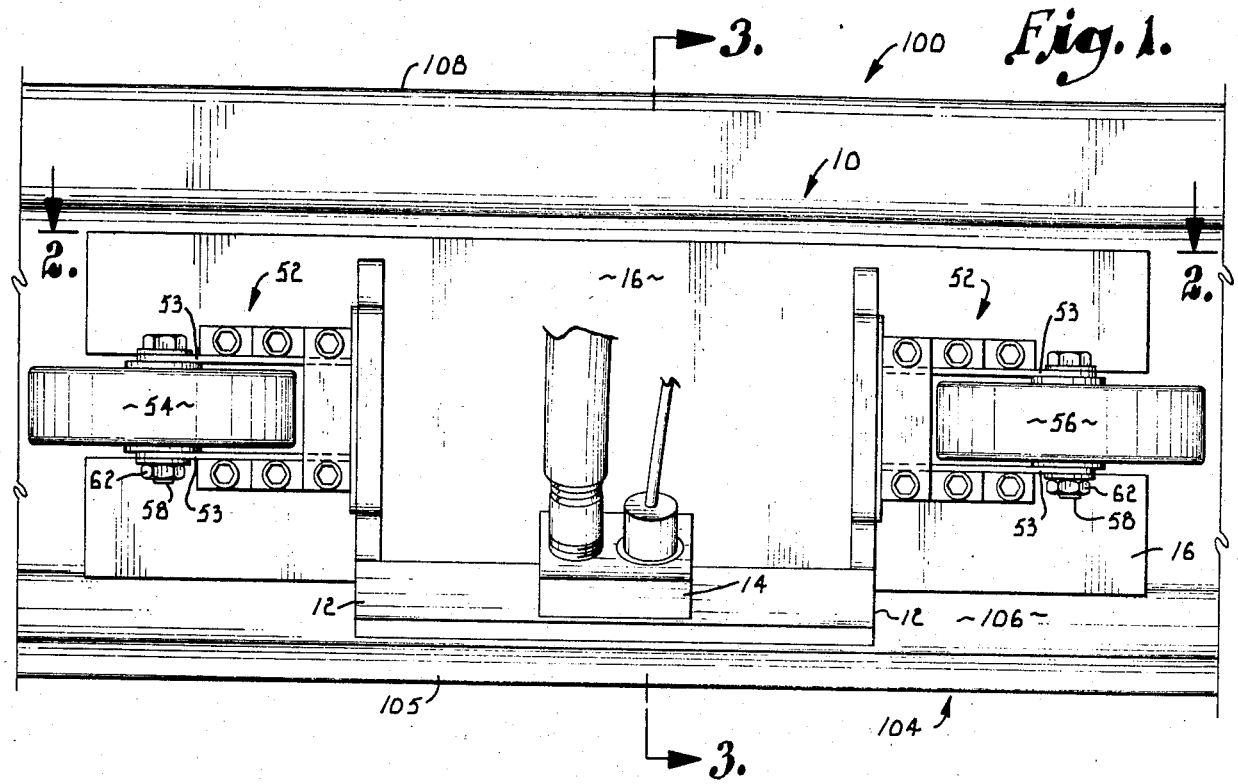
FIG. 1 is a sectional elevation view showing a portion of a track rail with the ultrasonic detection assembly disposed in a functional relationship thereon.
Figure 2:
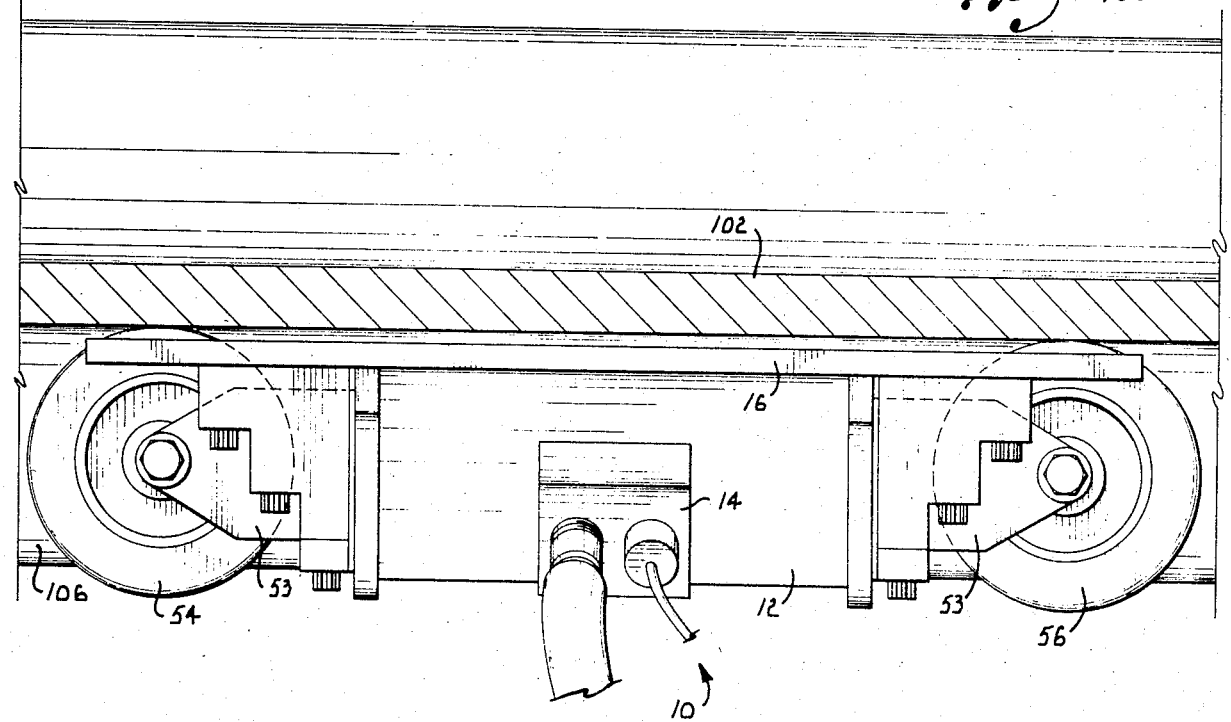
FIG. 2 is a sectional view, taken along line 2—2 in FIG. 1, and showing the cooperation of the roller members of the mounting plate with the web of the rail.

Turning more particularly to the drawings, FIG. 1 generally illustrates the detection apparatus 10 as comprising a sliding shoe 12 in the form of a rectangular plate with a housing 14 mounted thereon. Attached to the sliding plate 12 is a wheel mounting plate 16 disposed thereto so that plate 16 lies generally parallel to the web 102 of the rail 100 which in turn positions the sliding plate 12 in a proper relationship atop the top surface 106 of rail base 104.

Mounted to the mounting plate 16 by means of brackets 52 are first and second wheel members 54, 56. Shafts 58 extend through the opposed spaced-apart flanges 53 of each bracket 52 so as to present an axle for each wheel 54, 56. Nut 62/shaft 58 combination secures each shaft 58 to the flanges 53 of each bracket 52. Each wheel 54, 56 is peferrably disposed in a generally normal relationship to the web 102 of the rail 100 which extends between running surface 108 and rail base 104 as best seen in FIG. 3. This relationship provides rolling movement of the wheels 54, 56 and mounting plate 16, relative to web 102, in a spaced-apart relationship therebetween. Concurrent with such rolling movement is movement of sliding plate 12 along the top surface 106 of the rail base 104.

Housing 14 is generally shown in FIGS. 1-4 as comprising first and second compartments 18, 20 functionally referred to as a transducer compartment 18 and fluid compartment 20. A transducer unit 22 includes a housing 24 having an appropriate crystal element 26 therein. The housing 24 is nested within a brass sleeve 28 extending through the first transducer compartment 18 of the housing 14. Upon insertion of the housing 24 within the sleeve 28, the transducer element is in an unobstructed facing relationship with the top surface 106 of rail base 104 by means of an aperture 13 in sliding plate 12. A cable 30 extends from the transducer housing 24 for connection with associated signal-monitoring circuitry as illustrated in FIG. 1 of my incorporated patent.

The second fluid compartment 20 has a bore 31 extending therethrough with a fluid hose 32 received therein and connected to a fluid source (not shown). Water or any suitable coupling fluid medium is conveyed through this fluid hose 32 for injection through bore 31 and underneath the sliding plate, via plate aperture 13, into an interposition between the now spaced-apart sliding plate 12 and the top surface 106 of rail base 104. Accordingly, a conventional coupling medium is presented between the transducer 22 and top surface 106 of the rail which presents ultrasonic continuity and is effective in changing the angle of entry transmission of the search beams as digrammatically illustrated in FIG. 3 . so that said beams scrub the bottom surface 103 of rail base 104.

A more particular embodiment of the above discussed housing 14 is shown in FIGS. 8-10. Therein is shown a housing 114 having first 118 and second 120 compartments therein. Housing 114 is attached to sliding plate 12 by a screw 113/bracket 115 combination and is laterally adjustable thereon by means of relative positioning of slots 117 in each bracket 115 with similar apertures (not shown) in the sliding plate 12. The first transducer compartment 118 receives a block 136 with a brass sleeve 138 secured therein. O-rings 140 surround a transducer housing 124 so that the transducer unit 122 with communicating cable 130 can easily be slipped into the sleeve 138. The mounting block 136 is rotatably mounted about an axis extending through the compartment 118 as presented by a pin member 134 passing therethrough. A sheet rubber spring 142 extending between the the main housing 114 and mounting block 136 biases this block 136 and the transducer unit 122 therein in a clockwise direction as viewed in FIG. 10. An adjustment screw 144 extends through the housing 114 and contacts the mounting block 136 so as to bias the block 136 in a counterclockwise direction about the axis of pivot 134. The degree of extension of the screw 144 through housing 114 and onto block 136 effects the second bias thereon. Accordingly, the difference between the first and second biases produces a resulting bias which adjusts the position of the mounting block 136 relative to pin 134 and thus provides a user selectable inclination of the transducer unit 122 relative to the top surface 106.

The coupling fluid compartment 120 is in communication with a fluid source (not shown) via a flexible hose 148. As above discussed, opening 13 within the sliding plate 12 allows for the fluid to flow from compartment 120 onto the top surface 106 of the rail and into interposition between the rail top surface 106 and transducer 122 so as to provide a coupling medium therebetween. Depending from the mounting block 136 and partially surrounding the bottom of transducer unit 122 is an opaque shield 126. This shield diminishes reverberation of the coupling liquid wedge occurring between the transducer element 126 and top surface 106 of rail base 104.

A second embodiment 200 is as shown in FIG. 6. Therein a wheel 202 is rotatably mounted about axle 204. Surrounding the axle 204 is a sleeve 206 having a transducer element 208 attached thereto. Removable hubs 210 and 212 allow for user access within the wheel 202 so as to selectably direct the sleeve 206 and mounted transducer 208 towards the vertical wall 105 of the rail base 104. The wheel 200 is filled with a fluid coupling medium. In this embodiment a succession of signals are transmitted through the side walls 105 during relative rolling movement of the wheel 202 along the vertical wall 105 of the rail base. The associated transmitted and reflected signals are conveyed via cable 214 to monitor apparatus such as the type described in my U.S. Pat. No. 3,156,111.

A third embodiment 300 is as shown in FIG. 7 and again utilizes a fluid-filled wheel member 302 rotatably mounted about an axle 304 with such axle having a sleeve 306 mounted thereon. Transducer element 308 is affixed to this sleeve 306 and positioned so the transmitted signals are sent into the top surface 106 of the rail 100 and then directed along the base 103 thereof in a manner as diagrammatically illustrated in FIG. 7. Again, removable hubs 310, 312 allow for user access to sleeve 306 and transducer 308 to provide for a proper positioning thereof relative to the surface of rail base 104. The appropriate transmitted and reflected signals are conveyed to monitor apparatus via cable 314.

In all embodiments, relative movement of the transducer unit with the rail base 104 is provided. Thus, signals scrubbing the base are transmitted and reflected signals received along the longitudinal extent of the rail base 104 for monitoring by suitable monitor and/or detection apparatus. As more explicitly set forth in my incorporated U.S. Pat. No. 3,156,111, an ultrasonic machine is controlled by output pulses of a regenerator for reducing periodically recurring sets of echo signals. This ultrasonic machine is connected to the appropriate electro-mechanical transducer which is positioned in wave transmitting and receiving relationship with the rail base 104 as above described. Test signals are periodically applied through the transducer to provide reflected signals from the rail base 104 which are designated on the appropriate monitor. If internal discontinuities are present in the tested area of the rail base it will provide a reflected signal which will vary from the transmitted signal sent therein. Accordingly, the operator by viewing the associated monitor can ascertain whether there are any differences between the transmitted and received signals which correspond to defects in the rail. Upon such detection, the location of the defect, relative to the length of the rail, can then be ascertained and appropriate maintenance measures can then be taken.

It is also here noted that utilization of the apparatus of FIGS. 3 and 7 does not test the entire rail base 106. Accordingly, such apparatus 10, 300, as above described, are put in a side-by-side relationship on opposed sides of the web 102 so that opposing search signals may scrub the entire rail base.

Also, in reference to relative rail movement it is understood that the disclosed apparatus 10, 200, 300, may be fixed with the track rail 100 moving relative thereto or may be moveable along the extent of the track rail 100 with the track rail 100 staying in place. Either method can be employed with similar accompanying advantages and results.

It is to be understood that while certain forms of this invention have been illustrated and described, it is not limited thereto, except in so far as such limitations are included in the following claims.

I claim:

1. Apparatus for use in an ultrasonic determination of defects along the base of a track rail comprising:
   a sliding plate positioned on a top surface of said base of a rail;
   means for providing relative movement between said sliding plate and said top surface and along the longitudinal extent of said track rail;
   a housing mounted to said sliding plate, said housing comprising:
      a first compartment for receiving a transducer means therein;
      a mounting block for said transducer means positioned in said first compartment;
      means for rotating said mounting block about an axis passing therethrough with said rotation variously inclining said transducer means relative to said top surface; and
      means for maintaining said rotatable mounting block at a selected position relative to said axis whereby said transducer means is positioned at a selected inclination relative to said top surface;
   means for acoustically coupling said mounted housing with said top surface of said rail;
   said transducer means being a part of an ultrasonic testing system and mounting in said housing at a selected inclination relative to said top surface of said rail upon rotation of said mounting block;
   monitor means associated with said transducer means for checking signals transmitted and received by said transducer,
   said transducer means transmitting signals through said top surface of said rail and in a direction along the bottom surface of said rail base and receiving reflected signals resulting from said transmitted signals, said slidable plate movement presenting a succession of positions of said transducer means along the extent of said top surface of said rail base whereby to provide a plurality of transmitted and reflected signals therealong for delivery to said monitor means with said signals being useful in said determination of deflects along the base of a track rail.

2. The apparatus as claimed in claim 1, wherein said coupling means comprises an aperture in said sliding plate to physically present said top of said rail to said housing and said transducer means mounted therein.

3. The apparatus as claimed in claim 1, wherein said relative movement means comprises:
   a mounting plate attached to said sliding plate in a position facing a web of said track rail extending between said top surface of said rail base and a running surface of said track rail;
   at least one roller member rotatably mounted to said mounting plate and contacting said web with movement of said roller member along the longitudinal extent of said web providing for said relative sliding movement between said attached sliding plate and said top surface.

4. The apparatus as claimed in claim 1, further comprising:
   means for interposing a fluid between said transducer means and said top surface to provide an ultrasonic coupling medium therebetween.

5. The apparatus as claimed in claim 4, wherein said fluid means comprises:
   a fluid source; and
   means for conveying said fluid to said housing for subsequent delivery to said top surface of said rail via said coupling means whereby said fluid is interposed between said top surface and said sliding plate and said transducer means.

6. The apparatus as claimed in claim 1, wherein said rotating means is provided by a pin member extending through said first compartment and said mounting block, said block being rotatably mounted about said pin.

7. The apparatus as claimed in claim 1, wherein said maintaining means comprises:
   a first bias member associated with said housing and mounting block for urging said mounting block in a first direction about said axis of rotation;
   a second bias member associated with said housing and mounting block for urging said mounting block in a second direction about said axis of rotation opposite said first direction; and
   means for adjusting the relative difference between said biases to present an overall bias positioning said mounting block and transducer means therein at a selected position relative to said axis of rotation.

8. The apparatus as claimed in claim 7, wherein said first bias means comprises a spring member extending between said housing and mounting block to urge said block in said first direction.

9. The apparatus as claimed in claim 8, wherein said second bias means comprises an adjustable screw member extending through said housing and contacting said mounting block at a location to urge said block about said axis of rotation in said second direction wherein the adjustment of said screw in one direction increases said second bias on said mounting block and in an opposed direction decreases said second bias thereon.

10. The apparatus as claimed in claim 1, wherein said housing further comprises:
a second compartment positioned in a side-by-side relationship with said first compartment, said second compartment being in fluid communication with said first compartment;
a fluid source; and
conduit means for conveying said fluid from said fluid source to said second compartment, said fluid flowing into said first compartment and onto said top surface via said coupling means, said fluid being interposed between said top surface and said transducer means to act as an ultrasonic coupling medium therebetween.

11. Apparatus for use in an ultrasonic determination of defects along the base of a track rail comprising:
a sliding plate positioned on a top surface of said base of a rail;
a mounting plate attached to said sliding plate in a position facing a web of said track rail extending between said top surface of said rail base and a running surface of said track rail;
at least one roller member rotatably mounted to said mounting plate and contacting said web with movement of said roller member along the longitudinal extent of said web providing for relative sliding movement between said attached sliding plate and said top surface;
a housing mounted to said sliding plate;
means for acoustically coupling said mounted housing with said top surface of said rail;
transducer means being a part of an ultrasonic testing system and mounted in said housing at a selected inclination relative to said top surface of said rail;
monitor means associated with said transducer means for checking signals transmitted and received by said transducer,
said transducer means transmitting signals through said top surface of said rail and in a direction along the bottom surface of said rail base and receiving reflected signals resulting from said transmitted signals, said sliding plate movement presenting a succession of positions of said transducer means along the extent of said top surface of said rail base whereby to provide a plurality of transmitted and reflected signals therealong for delivery to said monitor means with said signals being useful in said determination of defects along the base of a track rail.

12. The apparatus as claimed in claim 11, wherein said acoustical coupling means comprises an aperture in said sliding plate to physically present said top of said rail to said transducer means.

13. The apparatus as claimed in claim 11, further comprising:
means for interposing a fluid between said transducer means and said top surface to provide an ultrasonic coupling medium therebetween.

14. The apparatus as claimed in claim 13, wherein said fluid means comprises:
a fluid source; and
means for conveying said fluid to said housing for subsequent delivery to said top surface of said rail via said acoustical coupling means whereby said fluid is interposed between said top surface and said sliding plate and said transducer means.

15. The apparatus as claimed in claim 11, wherein said housing comprises:
a first compartment for receiving said transducer means therein;
a mounting block for said transducer means positioned in said first compartment;
means for rotating said mounting block about an axis passing therethrough with said rotation variously inclining said transducer means relative to said top surface; and
means for maintaining said rotatable mounting block at a selected position relative to said axis whereby said transducer means is positioned at said selected inclination relative to said top surface.

16. The apparatus as claimed in claim 15, wherein said rotating means is provided by a pin member extending through said first compartment and said mounting block, said block being rotatably mounted about said pin.

17. The apparatus as claimed in claim 16, wherein said maintaining means comprises:
a first bias member associated with said housing and mounting block for urging said mounting block in a first direction about said axis of rotation;
a second bias member associated with said housing and mounting block for urging said mounting block in a second direction about said axis of rotation opposite said first direction; and
means for adjusting the relative difference between said biases to present an overall bias positioning said mounting block and transducer means therein at a selected position relative to said axis of rotation.

18. The apparatus as claimed in claim 17, wherein said first bias means comprises a spring member extending between said housing and mounting block to urge said block in said first direction.

19. The apparatus as claimed in claim 18, wherein said second bias means comprises an adjustable screw member extending through said housing and contacting said mounting block at a location to urge said block about said axis of rotation in said second direction wherein the adjustment of said screw in one direction increases said second bias on said mounting block and in an opposed direction decreases said second bias thereon.

20. The apparatus as claimed in claim 15, wherein said housing further comprises:
a second compartment positioned in a side-by-side relationship with said first compartment;
a fluid source; and
conduit means for conveying said fluid from said fluid source to said second compartment and onto said top surface via said coupling means, said fluid being interposed between said top surface and said transducer means to act as an ultrasonic coupling medium therebetween.

* * * * *